US00PP33131P2

(12) United States Plant Patent
Danziger

(10) Patent No.: US PP33,131 P2
(45) Date of Patent: Jun. 1, 2021

(54) ***COREOPSIS* PLANT NAMED 'DCORSOSB'**

(50) Latin Name: *Coreopsis grandiflora*
Varietal Denomination: DCORSOSB

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 16/919,797

(22) Filed: Jul. 2, 2020

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 6/14
See application file for complete search history.

*Primary Examiner* — Anne Marie Grunberg
(74) *Attorney, Agent, or Firm* — Cassandra Bright

(57) ABSTRACT

A new and distinct cultivar of *Coreopsis* plant named 'DCORSOSB' is disclosed, characterized by a unique very compact and mounded plant habit. Flowering begins early. Ray florets are distinctively yellow with a red base and red flush. Red coloration is more pronounced in cooler temperature and less intense light conditions. The new variety is a *Coreopsis*, normally produced as an outdoor garden or container plant.

3 Drawing Sheets

Latin name of the genus and species: *Coreopsis grandiflora.*

Variety denomination: 'DCORSOSB'.

BACKGROUND OF THE INVENTION

The new *Coreopsis* cultivar is a product of a planned breeding program conducted by the inventor, Gavriel Danziger in Moshav Mishmar Hashiva, Israel. The objective of the breeding program was to produce new *Coreopsis* varieties for ornamental purposes. The open pollination resulting in this new variety was made during Spring of 2016.

The seed parent is the unpatented, propriety variety referred to as *Coreopsis* 'COR 103'. The pollen parent is unknown as it was an open pollination breeding program. The new variety was discovered in July of 2017 by the inventor in a group of seedlings resulting from the 2016 open pollination, in a greenhouse in Moshav Mishmar Hashiva, Israel.

Asexual reproduction of the new cultivar 'DCORSOSB' was first performed by terminal vegetative cuttings during February 2018, at a greenhouse in Moshav Mishmar Hashiva, Israel. Subsequent propagation by vegetative cuttings has shown that the unique features of this cultivar are stable and reproduced true to type in more than 6 successive generations. Date of first sale was Jul. 6, 2019, occurring in the Netherlands. This sale was made directly by the inventor or one who obtained the claimed invention directly or indirectly from the inventor. This sale and all public disclosures made between Apr. 7, 2019 and the filing of this application fall within the exception allowed under 102(b)(1).

SUMMARY OF THE INVENTION

The cultivar 'DCORSOSB' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCORSOSB' These characteristics in combination distinguish 'DCORSOSB' as a new and distinct *Coreopsis* cultivar:

1. Unique very compact and mounded plant structure.
2. Early flowering.
3. Ray florets are yellow with a red base and red flush. Red coloration is more pronounced in cooler temperature and less intense light conditions.

PARENT COMPARISON

Plants of the new cultivar 'DCORSOSB' are similar to plants of the seed parent, most horticultural characteristics, however, plants of the new cultivar 'DCORSOSB' differ in the following;

1. Plant habit of the new variety is compact and mounded, the seed parent is an upright plant.
2. New variety is shorter than the seed parent.
3. Plant structure of the new variety is uniformly radial, plant structure of the seed parent amorphous.
4. The new variety has larger flowers than the seed parent.
5. The new variety has shorter peduncles than the seed parent.

COMMERCIAL COMPARISON

Plants of the new cultivar 'DCORSOSB' can be compared to the patented commercial variety *Coreopsis* 'DCOREO16' U.S. Plant Pat. No. 25,241. These varieties are similar in most horticultural characteristics; however, 'DCORSOSB' differs in the following:

1. The new variety has bi-color yellow and red ray florets, ray florets of this comparator are sold yellow.

2. The new variety has lighter green foliage than this comparator.
3. Flowers of the new variety are single; flowers of this comparator are fully double.

Plants of the new cultivar 'DCORSOSB' can also be compared to the patented commercial variety *Coreopsis* 'Sundancer' U.S. Plant Pat. No. 7,823. These varieties are similar in most horticultural characteristics; however, 'DCORSOSB' differs in the following:

1. Flowers of the new variety are single, flowers of this comparator are semi-double.
2. The new variety has shorter peduncles than this comparator.
3. Plant form of the new variety is very compact and round, plant form of this comparator is spreading.

BRIEF DESCRIPTION OF THE PHOTOGRAPHS

The accompanying photograph in FIG. 1 illustrates in full color a typical plant of 'DCORSOSB' grown in a 12 cm pot outdoors in Moshav Mishmar Hashiva, Israel under hot, bright Summer conditions.

Figure 1:
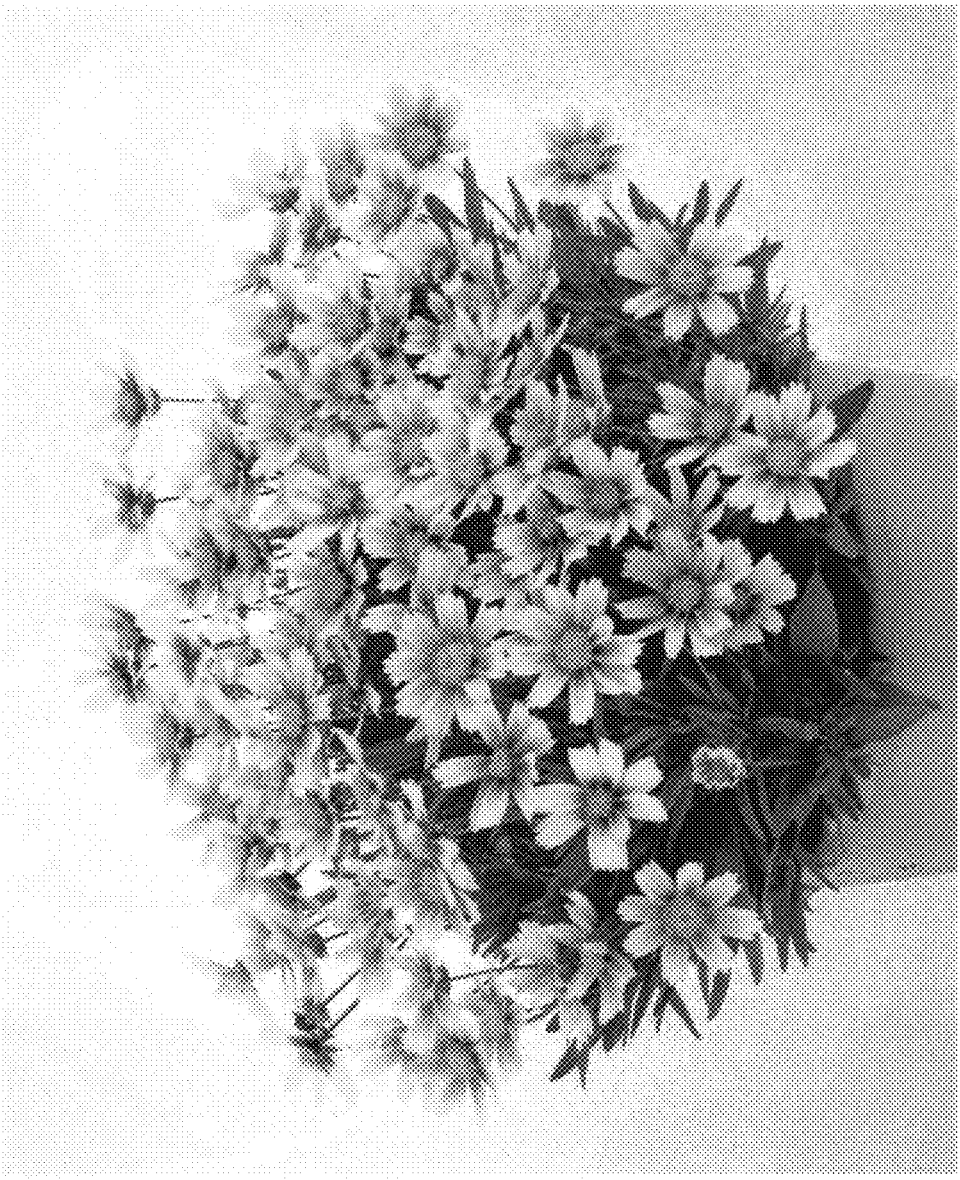
Figure 2:
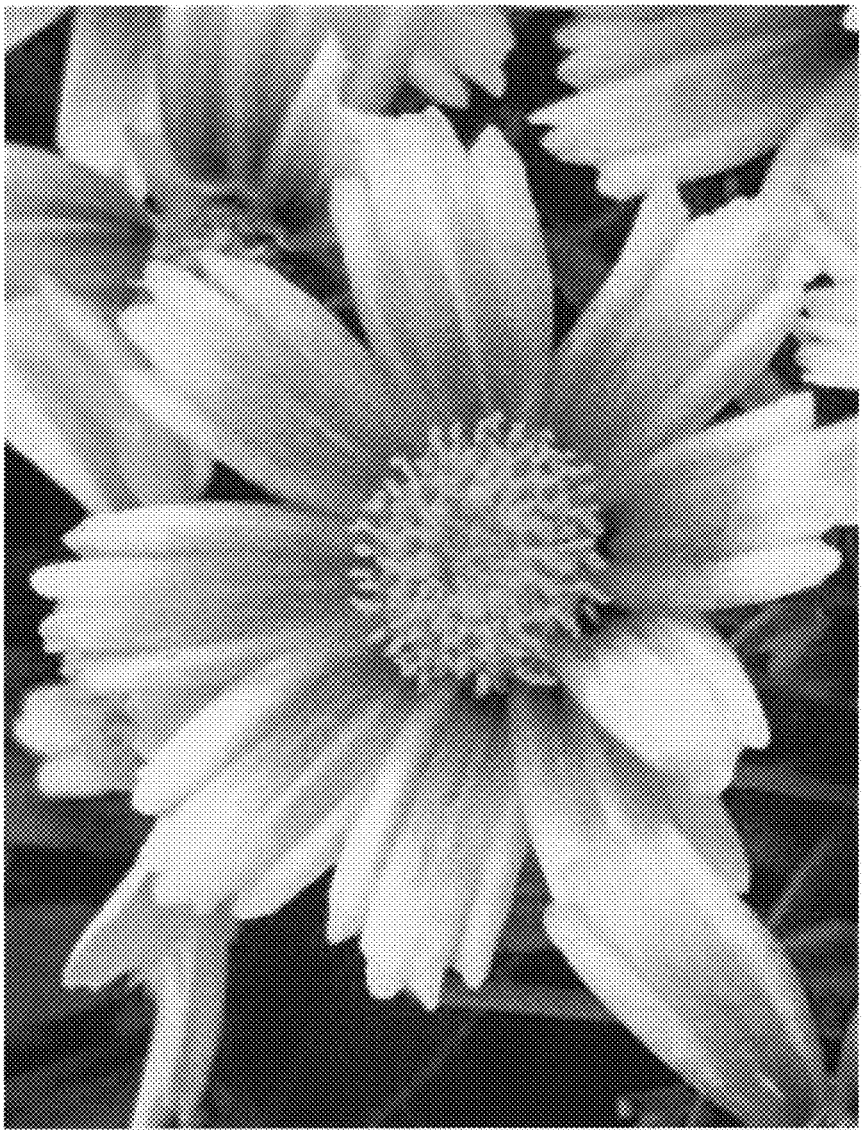
FIG. 2 illustrates in full color a typical inflorescence of 'DCORSOSB' grown under hot, bright, Summer conditions. Age of the plant photographed is approximately 11 weeks from a rooted cutting in a 12 cm pot.
Figure 3:
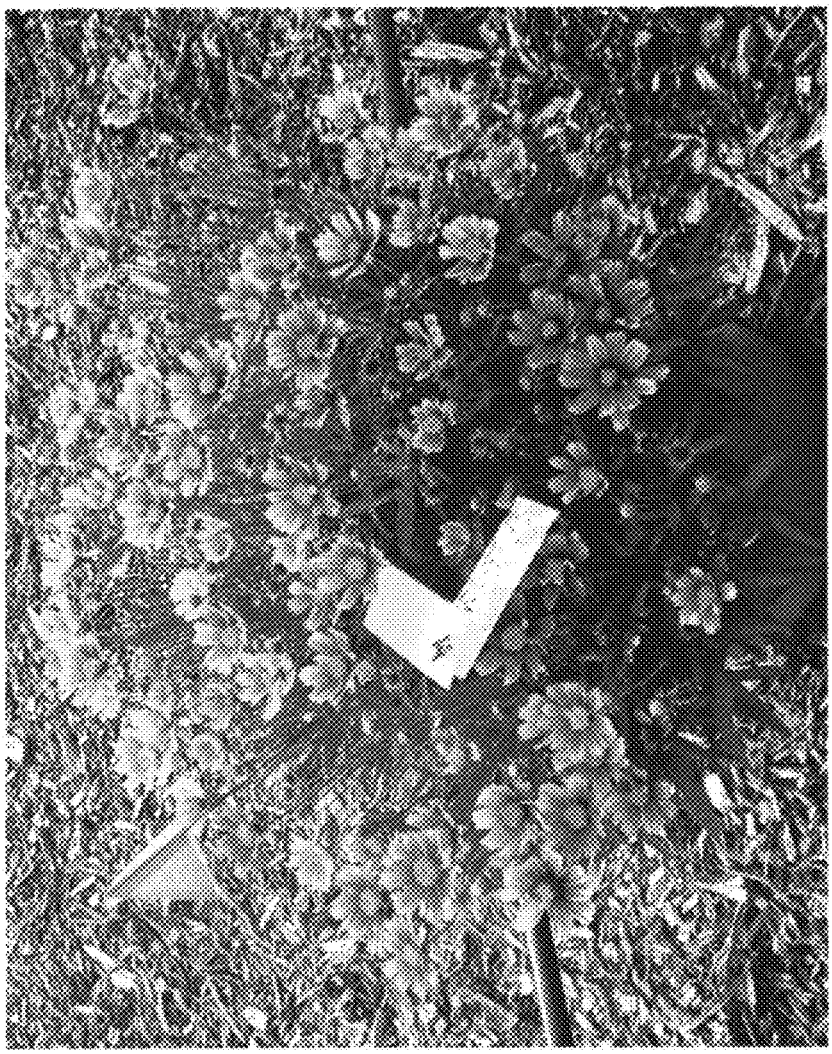
FIG. 3 illustrates a plant grown during early Spring under cooler conditions.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCORSOSB' plants grown in a greenhouse in Moshav Mishmar Hashiva, Israel, under natural lighting. Measurements were taken during April of 2016. The plants were approximately 60 days old from a rooted cutting in a 12 cm pot. The growing temperature ranged from approximately 18° C. to 28° C. during the days, 13° C. to 18° C. during the nights. Measurements and numerical values represent averages of typical plant types. Measurements taken during June of 2020.

Botanical classification: *Coreopsis grandiflora* 'DCORSOSB'.

PROPAGATION

Total rooting time: About 14 days at approximately 25° C. for a fully rooted cutting.

Root description: Well branched. Fleshy and white, color not accurately measured with R.H.S. chart.

PLANT

Growth habit: Very compact and mounded.

Height: Approximately 28 cm.

Plant spread: Approximately 30 cm.

Growth rate: Moderate.

Branching characteristics: Well branched, basal branching.

Length of lateral branches: Approximately 16 cm.

Diameter of lateral branches: Approximately 0.3 cm.

Texture of lateral branches: Glabrous.

Internodes length: Approximately 3.0 cm.

Strength of stem: Flexible and strong, not likely to break.

Color of lateral branches: Near Green 143C.

Aspect/angle of branches: Straight, occurring at approximately 45 degree from plant center.

Number of leaves per lateral branch: Approximately 15 to 20.

FOLIAGE

Leaf:

*Arrangement*.—Sub opposite or whorled from base.
*Average length*.—Approximately 5 to 6 cm.
*Average width*.—Approximately 0.7 cm.
*Shape of blade*.—Oblanceolate.
*Apex*.—Acute.
*Base*.—Acuminate.
*Attachment*.—Sessile.
*Margin*.—Entire.
*Texture of top surface*.—Very light and delicate hair.
*Texture of bottom surface*.—Glabrous.
*Appearance top surface*.—Matte.
*Appearance bottom surface*.—Matte.
*Color*.—Young foliage upper side: Near Yellow-Green 144A. Young foliage under side: Near Green 143C. Mature foliage upper side: Near Green 137A. Mature foliage under side: Near Green 138B.
*Venation*.—Type: Reticulate. Venation color upper side: Near Green N137A. Venation color under side: Near Green 137A.

FLOWER

Bloom period: In moderate climate zones, USDA Zone 7 and up blooming occurs from Spring to late Fall. In cooler climate zones from Summer until Fall.

Bud:

*Bud shape*.—Oblate.
*Bud length*.—Approximately 0.5 cm.
*Bud diameter*.—Approximately 0.7 cm.
*Bud color*.—Near Yellow-Green N144B.

Inflorescence:

*Form*.—Composite.

Flower:

*Diameter of entire flower*.—Approximately 4.5 cm.
*Depth of flower*.—Approximately 1.5 cm.
*Diameter of disc*.—Approximately 1.1 cm.
*Depth of disc*.—Approximately 0.4 cm.

Ray florets:

*Number of ray florets*.—8 Avg.
*Length*.—Approximately 2.3 cm.
*Width*.—Approximately 1.2 cm.
*Apex shape*.—3 to 5 truncate lobes.
*Base*.—Tapered.
*Margin*.—Entire.

Color:

*Ray florets*.—Upper surface at first opening: Near Yellow 7A, base strongly Red 53A. In cooler temperatures, about 50% of the base is red, and a red flush extends almost the entire ray floret. In warmer, brighter conditions about 20% of the base is red.

Upper surface at maturity: Near Yellow 7A, base Red 53B. In cooler temperatures, about 30% of the base is red and a red flush extends over about 70% of the ray floret. In warmer, brighter conditions about 20% of the base is red. Upper surface at fading: Near Yellow 8B, base strongly flushed Red 47C. In cooler temperatures, about 20% of the base is flushed red. In warmer, brighter conditions about 50% of the base is flushed red. Under surface at first opening: Near Yellow 9A. Under surface at maturity: Near Yellow 7B. Under surface at fading: Near Yellow 7B.

Disc florets:

*Number of disc florets*.—Approximately 80.

*Length*.—Approximately 1.0 cm.

*Width*.—Approximately 0.2 cm.

*Shape*.—Tubular with 5 lobes on tip.

*Margin*.—Entire.

*Color*.—At first opening: Near Yellow-Orange 15A. At maturity: Near Yellow-Orange 15B. At fading: Near Yellow-Orange 16B.

Fragrance: Very delicate, sweet scent.

Phyllaries/involucral bracts:

*Number*.—Approximately 8.

*Sepal length*.—Approximately 1.2 cm.

*Sepal width*.—Approximately 0.5 cm.

*Sepal texture*.—Glabrous.

*Apex shape*.—Acute.

*Margin*.—Entire.

*Color*.—Near Yellow 9A.

Peduncle:

*Peduncle length*.—Approximately 10 cm.

*Peduncle diameter*.—Approximately 0.15 cm.

*Angle*.—Approximately 90 degree from center of whorl.

*Color*.—Near Green 137C.

*Strength*.—Flexible

*Peduncle texture*.—Glabrous. .

REPRODUCTIVE ORGANS

Disc florets:

*Androecium*.—Present, Androecium of 5 stamens, these fused by their anthers, surrounding the style. Anther shape: Linear and flat. Anther length: Approximately 0.1 cm. Anther color: Near Yellow-Orange 14B. Pollen quantity: Moderate.

*Gynoecium*.—Present, ovary inferior, gynoecium of two fused carpels. Pistil number: 1 per floret. Pistil shape: Cylindrical oblong tube with two branched at tip. Pistil length: Approx. 0.5 cm. Style length: Approx. 0.3 cm. Style color: Near Yellow-Green 151D. Stigma shape: V shaped with two, curved downward, branched-at tip. Stigma color: Near Yellow 12A. Ovary Length: 0.1 cm. Ovary color: Near Yellow-Green 149D.

Ray florets:

*Androecium*.—Not present.

*Gynoecium*.—Pistil length: Approx. 1 cm. Style length: Approx. 0.7 cm. Style color: Near RHS Yellow-Green 150A. Stigma shape: V Shape. Stigma color: Near RHS Yellow-Orange 17A. Ovary diameter: 0.2 cm. Ovary color: Near RHS Yellow-Green 149D.

OTHER CHARACTERISTICS

Seeds and fruits: Not observed.

Disease/pest resistance: Neither resistance nor susceptibility to the normal diseases and pests of *Coreopsis* have been observed. Pests common to *Coreopsis* include Aphids and thrips. Typical diseases are *Botrytis* and *Pythium*.

Temperature tolerance: To USDA Zone 5.

Other tolerance: Tolerant to hot, humid Summer climates.

What is claimed is:

1. A new and distinct cultivar of *Coreopsis* plant named 'DCORSOSB' as herein illustrated and described.

* * * * *